United States Patent [19]

Brace et al.

[11] Patent Number: 5,051,645

[45] Date of Patent: Sep. 24, 1991

[54] ACOUSTIC WAVE $H_2O$ PHASE-CHANGE SENSOR CAPABLE OF SELF-CLEANING AND DISTINGUISHING AIR, WATER, DEW, FROST AND ICE

[75] Inventors: John G. Brace, Brown Deer; Thomas S. Sanfelippo, Milwaukee, both of Wis.

[73] Assignee: Johnson Service Company, Milwaukee, Wis.

[21] Appl. No.: 472,125

[22] Filed: Jan. 30, 1990

[51] Int. Cl.$^5$ ............................................. H01L 41/08
[52] U.S. Cl. ............................ 310/313 D; 310/313 R; 73/579
[58] Field of Search ................ 310/313 D, 313 R; 340/580–582, 602–604; 73/579; 333/152, 153

[56] References Cited

U.S. PATENT DOCUMENTS

| | | | |
|---|---|---|---|
| 3,465,535 | 9/1969 | Dodge, III | 62/151 |
| 3,641,781 | 2/1972 | Nijo | 62/151 |
| 3,689,907 | 9/1972 | Guajardo | 340/602 |
| 3,995,240 | 11/1976 | Kerbel | 333/153 |
| 4,037,427 | 7/1977 | Kramer | 62/128 |
| 4,102,207 | 7/1978 | Frost et al. | 73/643 |
| 4,121,433 | 10/1978 | Pomerantz | 62/140 |
| 4,126,047 | 11/1978 | Sethares et al. | 73/505 |
| 4,176,524 | 12/1979 | Kamiyama et al. | 62/140 |
| 4,206,612 | 6/1980 | Gardner | 62/128 |
| 4,270,105 | 5/1981 | Parker et al. | 310/313 A |
| 4,312,228 | 1/1982 | Wohltjen | 310/313 R |
| 4,342,971 | 8/1982 | Councilman et al. | 333/152 |
| 4,347,709 | 9/1982 | Wu et al. | 62/140 |
| 4,348,869 | 9/1982 | Massa | 62/140 |
| 4,404,852 | 9/1983 | Goto | 73/599 |
| 4,530,218 | 7/1985 | Janke et al. | 62/156 |
| 4,532,806 | 8/1985 | Bruchmüller | 340/582 |
| 4,568,922 | 2/1986 | Schwippert et al. | 340/582 |
| 4,604,612 | 8/1986 | Watkins et al. | 340/582 |
| 4,661,738 | 4/1987 | Skeie | 310/313 D |
| 4,681,855 | 7/1987 | Huang | 436/39 |
| 4,818,961 | 4/1989 | Takahashi et al. | 333/194 |
| 4,878,036 | 10/1989 | Yatsuda et al. | 310/313 D |
| 4,891,628 | 1/1990 | Zuckerman | 340/582 |
| 4,960,329 | 10/1990 | Schofield | 356/5 |

FOREIGN PATENT DOCUMENTS

| | | |
|---|---|---|
| 2730648 | 1/1979 | Fed. Rep. of Germany . |
| 0125105 | 10/1981 | Japan ............... 310/313 R |
| 0147317 | 7/1987 | Japan ............... 310/313 R |
| 63-221233 | 9/1988 | Japan . |
| 0263810 | 10/1988 | Japan ............... 310/313 R |
| 1173185 | 8/1985 | U.S.S.R. ................ 73/579 |
| 1201687 | 12/1985 | U.S.S.R. ................ 73/579 |

OTHER PUBLICATIONS

Hughes et al., "Liquid–Solid Phase Transition Detection with Acoustic Plate Mode Sensors: Application to Icing of Surfaces", *Sensors and Actuators*, A21–A23 (1990) pp. 693–699.

Hafeez, et al., "Ice Dectection using Surface Acoustic Waves", *Acta Polytechnica Scandinavica*, Applied Physics Series No. 118, Helsinki 1977, pp. 3–10.

Clark, "Water Frost and Ice: The Near-Infrared Spectral Reflectance 0.65–2.5 $\mu m$", *Journal of Geophysical Research*, vol. 86, No. B4, Apr. 10, 1981, pp. 3087–3096.

Deom, et al., "Detection and Measurement of Ice Accretion on a Profile by an Ultrasonic Method", AIAA 25th Aerospace Sciences Meeting, AIAA-87-0179, Reno, Nev., Jan. 1, 1987, pp. 1–5.

Garnier, et al., "Capteur Ultrasonore pour la Detection et la Mesure d'Epaisseur de Givre sur un Profil", 2éme Colloque International sur la Sécurité Aérienne, Toulouse, Nov. 1986, pp. 1–10.

*Primary Examiner*—Mark O. Budd
*Assistant Examiner*—Thomas M. Dougherty
*Attorney, Agent, or Firm*—Foley & Lardner

[57] ABSTRACT

A surface-acoustic-wave (SAW) $H_2O$ phase-change sensor capable of distinguishing air, water, dew, frost and ice. The sensor can also distinguish various frost thicknesses. The sensor has a size allowing batch fabrication of the chips, and allowing the device to fit in small spaces such as between fins of an evaporator. The sensor is fabricated on a strong piezoelectric substrate with a short acoustic path length. The SAW phase-change sensor experiences large changes in insertion loss and impedance upon deposition of water in various phases. The sensor has a hydrophobic surface treatment covering the SAW sensor surface, and if placed in a vertical position will self-clean during a refrigeration defrost cycle.

22 Claims, 3 Drawing Sheets

ACOUSTIC WAVE H₂O PHASE-CHANGE SENSOR CAPABLE OF SELF-CLEANING AND DISTINGUISHING AIR, WATER, DEW, FROST AND ICE

BACKGROUND OF THE INVENTION

1. Field of the Invention

This invention relates to devices used for frost sensing in a "demand-defrost" refrigeration system. The device can be applied broadly to heatabsorbing surfaces and to measure surface condensation from the atmosphere. Typical heatabsorbing surfaces to which the sensor may be applied include an evaporator tube, fin or shell in a refrigerator or heat pump. Another typical surface on which surface condensation and accretion detection are important is an aircraft wing.

2. Description of the Prior Art

Previous frost sensors include capacitive, optical, and acoustical structures. Capacitive structures experience an increase in capacitance due to frost deposition between plates monitored. Optical modules experience attenuation or scattering of light due to frost deposition. Acoustical cavities or waveguides experience an attenuation of sound due to frost deposition.

All three frost detection methods have drawbacks. There is a lack of discrimination between frost and ice in capacitive or optical schemes. The lack of thermal contact to the evaporator may limit the accuracy of optical devices. The size of acoustic waveguides limits their direct placement within available spaces in an evaporator.

SUMMARY OF THE INVENTION

It is an object of this invention to create a frost sensor of small size which may be fabricated in batches such as integrated circuit chips. The small size allows a fit into closely spaced openings such as between fins of an evaporator for direct sensing of cold surfaces.

It is another object of this invention to create a frost sensor capable of discriminating between air, water, dew, frost, and ice. The frost sensor should also discriminate between frost thicknesses. The device should exhibit large signal changes, for relative ease of H₂O phase-change determination. Discrimination between H₂O phasechanges will allow shortening of a refrigeration defrost cycle.

It is another object of this invention to create a frost sensor with a hydrophobic surface. The hydrophobic surface will allow self-cleaning during defrost and protection from contaminants.

The present invention relates to a discovery that surface acoustic wave (SAW) devices exhibit high sensitivity to frost/ice deposition and to liquid/solid phase changes of H₂O. The present invention consists of a SAW phase-change sensor with short acoustic path length on a strong piezoelectric substrate. The sensor can be batch fabricated, and its small size allows placement in good thermal contact with a cold surface such as a refrigeration evaporator fin. The SAW phase-change sensor experiences large changes in insertion loss and a.c. impedance upon deposition of H₂O in various phase changes. The sensor has a hydrophobic surface treatment and placed in a vertical position will self-clean during a refrigeration defrost cycle.

BRIEF DESCRIPTION OF THE DRAWINGS

Further details of the present invention are explained with reference to the attached drawings in which.

DESCRIPTION OF THE PREFERRED EMBODIMENTS

A. The SAW Phase-Change Sensor

Figure 1A:
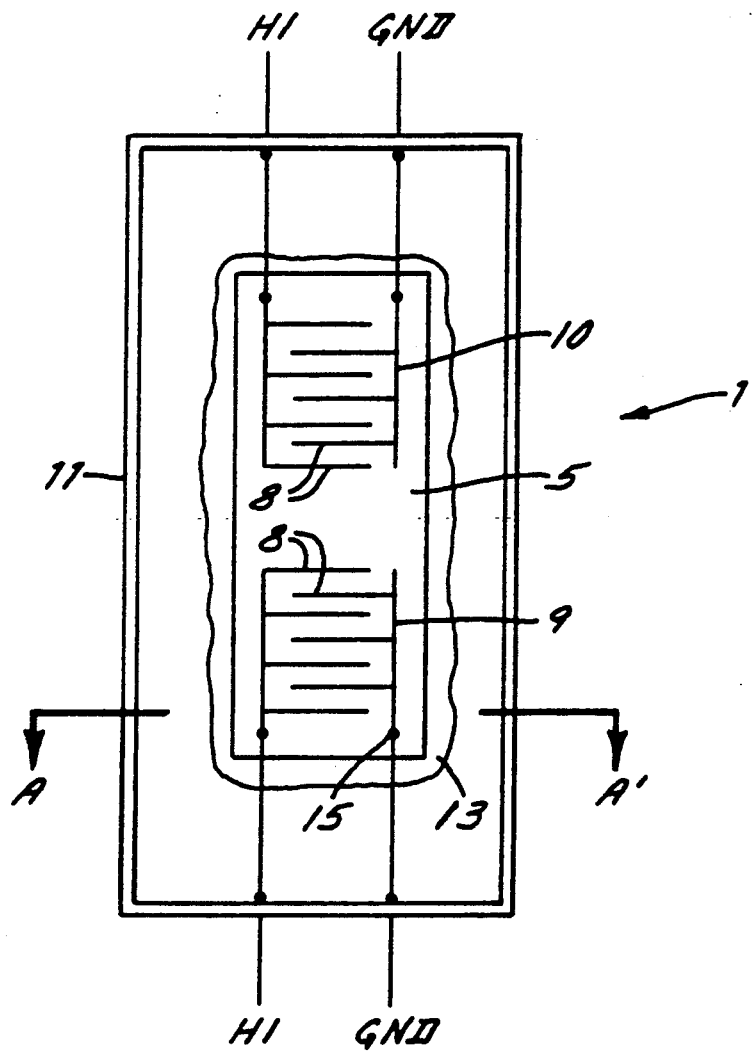
FIG. 1A shows a plan view of a SAW sensor made in accordance with the invention.
Figure 1B:
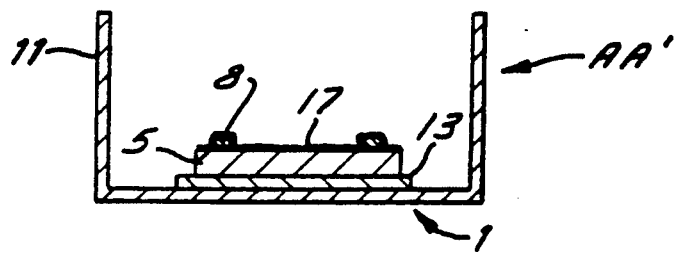
FIG. 1B shows a cross section of the SAW sensor of FIG. 1A taken along line A—A' thereof.

FIG. 1A shows the SAW phase-change sensor 1 of the present invention. FIG. 1B shows a cross sectional view of the sensor of FIG. 1A taken along line AA' of FIG. 1A. The thicknesses in FIG. 1B are not to scale. The SAW phase-change sensor 1 consists of a piezoelectric substrate 5, patterned metallization 8, a thermally conductive package 11, thermally conductive adhesive 13, wirebonds 15, and hydrophobic surface treatment 17.

As an example, a batch of sensors 1 was fabricated with X-propagation on a 128 degree rotated Y-cut lithium niobate substrate (128Y-X LiNbO₃). The lithium niobate thickness was 0.5mm. The metallization 8 was RF-diode sputtered Cr/Au (50Å/1000Å), and was patterned using conventional photolithography. The metallization patterns formed interdigitated transducers (IDT's) which were conventional λ/4 types with period λ=52.5μm and an aperture width w=2800μm. This yields a center frequency of approximately 75 MHz. One IDT serves as an input transducer indicated at 9 whereas the other IDT serves as an output transducer indicated at 10. As an example, the input IDT may have 10 finger pairs and the output IDT 30 finger pairs. Center-to-center spacing of the two IDTs was 30λ(1575μm). This spacing is quite small compared with many SAW designs, but is advantageous for lossymedium sensing applications because the short path length results in manageable total insertion loss. The ratio of substrate thickness to acoustical wavelength is typically 9 or higher so the Rayleigh propagation mode tends to dominate. After metallization and oscillation checks for every metallization pattern, a wafer which consists of approximately 80 metallization patterns was diced.

Once diced, the individual sensors 1 were individually mounted in gold-plated nickel thermally conductive packages, or flatpacks 11. The piezoelectric substrates were attached to flatpacks 11 using thermally conductive epoxy adhesive 13. The metallization patterns were then wirebonded at point 15 to make electrical connections to the flatpack. Finally, a hydrophobic surface treatment 17 was formed on the surface of each sensor by treating the metallization patterns with a polysiloxane derivatizer.

B. Self Cleaning Orientation

Figure 2:
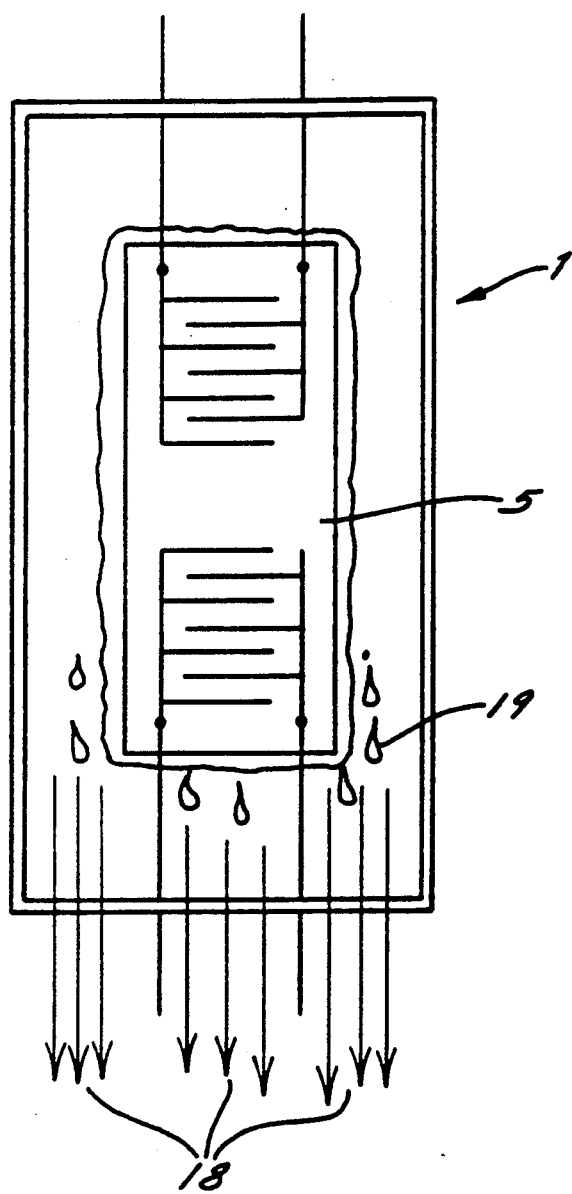
FIG. 2 illustrates the self cleaning orientation of the SAW phase-change sensor with hydrophobic surface treatment to repel liquid water.

FIG. 2 demonstrates the self cleaning orientation of the SAW phase-change sensor 1 with hydrophobic surface treatment to repel water, droplets of which are indicated at 19. The hydrophobic behavior is particularly advantageous when the sensor surface is oriented vertically, as demonstrated in FIG. 2 by the gravity direction lines 18. Being oriented vertically in simulated frost/defrost cycles, the water 19 which formed from melting frost or ice was drained from the sensor surface due to gravity 18 and the preferential wetting of surrounding surfaces. This effect is advantageous because the sensor tends to be self-cleaning when liquid is present, such as during a defrost cycle.

Even with the sensor mounted horizontally, the liquid will wet the flatpack surfaces, but will be repelled from the surface of sensor 1 by the hydrophobic surface treatment 17. During experimentation, 0.5 ml of distilled water added to the flatpack wetted the flatpack interior, but was repelled from the substrate 5 and formed an air bubble arching over the surface of substrate 5 which persisted about 10 s before collapsing.

C. Test Configuration

Figure 3A:
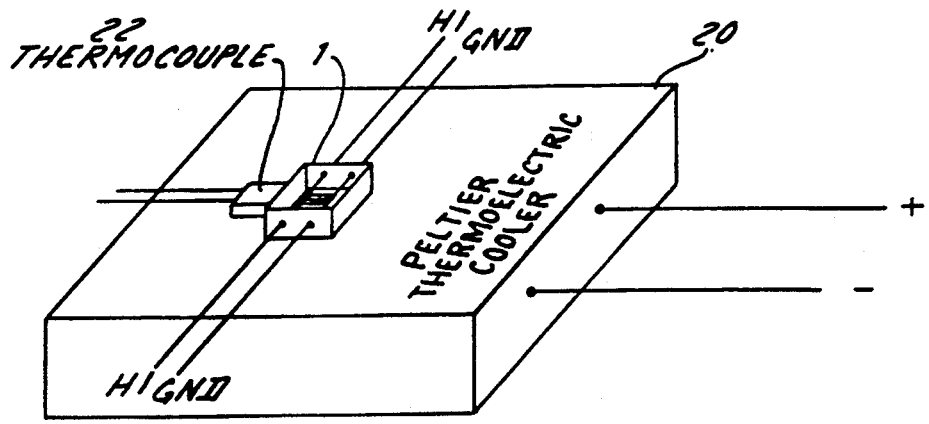
FIG. 3A shows the mounting of the SAW phase-change sensor of FIG. 1A in a simulation apparatus.

FIG. 3A illustrates a simulation apparatus used in testing the sensor 1 and is seen to include a Peltier thermoelectric cooler 20 for simulating an evaporator cold surface and a thermocouple 22 for measuring surface temperature. A SAW phase-change sensor 1 is mounted in thermal contact with one face of the Peltier thermoelectric cooler 20. Thermocouple 22 is placed in thermal contact with the flatpack 11.

Figure 3B:
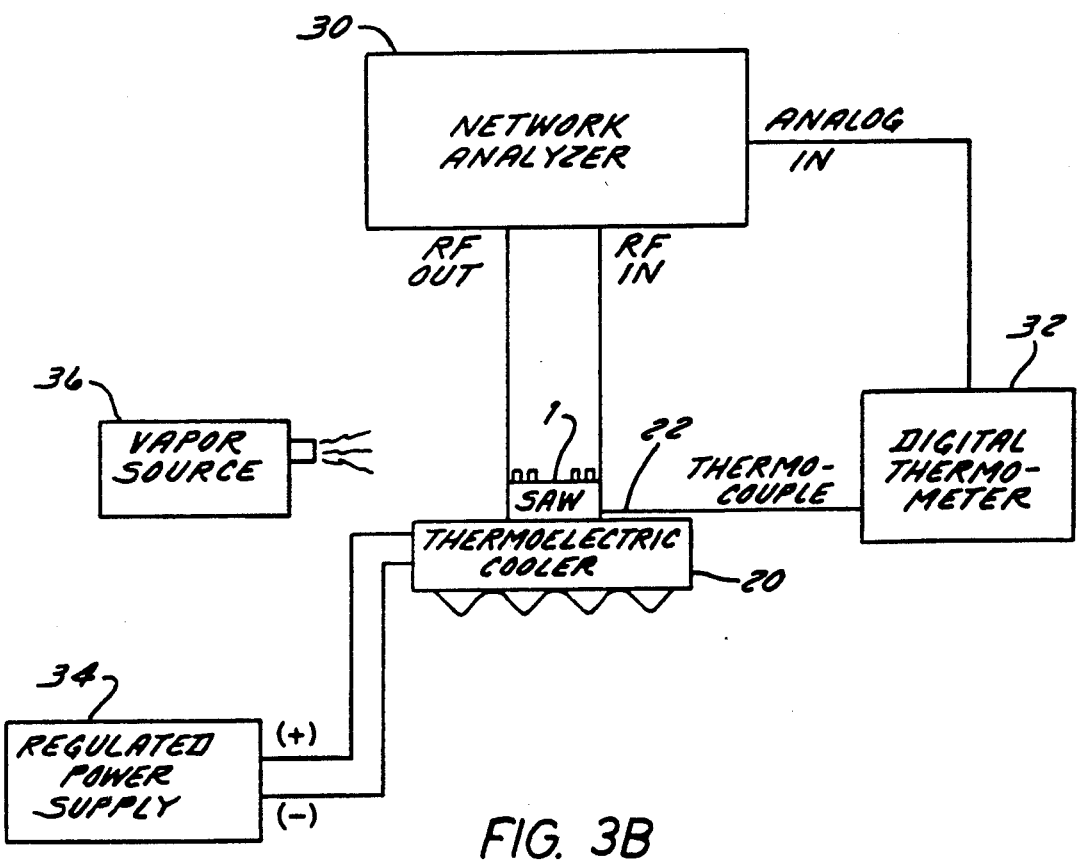
FIG. 3B shows a block diagram of test equipment configuration for testing the test setup of FIG. 3A.

FIG. 3B shows a block diagram of the test equipment configuration for testing the setup of FIG. 3A. A network analyzer 30 is connected to the SAW phase-change sensor 1 to measure transmission (insertion loss) and input reflection (impedance). A digital thermometer 32 is connected between the thermocouple and network analyzer 30. The network analyzer 30 also measures analog voltages from the digital thermometer 32 which provides voltage signals proportional to thermocouple 22 temperature. Surface temperature was varied by supplying dc power from a regulated power supply 34 to the Peltier thermoelectric unit 20. A vapor source 36 was provided to generate humid air. The vapor source 36 operated by bubbling compressed air through water and directing this saturated air stream toward the chilled sensor when dew or frost generation was required.

D. Air, Water, Dew and Frost Discrimination Tests

Table 1 summarizes initial measurements taken to confirm that the SAW phase-change sensor could distinguish between air, dew, water, and frost. Measurements were made using the configuration of FIG. 3B. Measurements were made with the SAW phasechange sensor surface horizontal. Transmission was measured from 65 MHz to 85 MHz with the minimum insertion loss and its corresponding frequency listed in Table 1. Table 1 tabulates the measurement results.

TABLE 1

| MEASURED INSERTION-LOSS RESPONSES | | | |
|---|---|---|---|
| Condition | Temp. (°C.) | Insertion Loss (dB) | Freq. (MHz) |
| air | +20.0 | 9.2 | 74.7 |
| water | −2.0 | 28.4 | 74.6 |
| dew | −2.0 | 21.7 | 74.4 |
| frost | −2.0 | 36.0 | 75.4 |

The first measurement for air shows an insertion loss of 9.2 dB at 74.7 MHz. Filling the flatpack with distilled water and chilling to −2° C. increased the insertion loss to 28.4 dB at 74.6 MHz. There is minimal shift in frequency of the peak, probably because only a very thin layer of water couples to the 75 MHz SAW. The supercooled water persists in liquid form for many minutes before freezing.

When the dry sensor is chilled in air, dew formation occurs to an extent dependent on the ambient dewpoint. There is no appreciable effect on insertion loss until the sensor surface temperature approaches the dewpoint. Insertion loss of the sensor due to dew deposited by chilling to −2° C. is 21.7 dB at 74.4 MHz. As is the case for bulk liquid water, supercooled dew persists for many minutes at −2° C. When the dew freezes, the acoustic response of the sensor is dramatic. With almost identical surface coverage of frost the insertion loss changes to 36.0 dB and the peak frequency shifts to 75.4 MHz, a substantial change for a SAW device.

Table 2 shows a compilation of multiple measurements made with SAW phase-change sensors fabricated as discussed hereinbefore to confirm that the SAW phase-change sensor could distinguish between air, dew, frost, and water. The insertion loss measurements in Table 2 were made using SAW phase-change sensors over the stated temperature range for each phase-change condition.

TABLE 2

| OVERVIEW OF INSERTION-LOSS MEASUREMENTS | | |
|---|---|---|
| Condition | Temp. (°C.) | Insertion Loss (dB) |
| air | −4 to +70 | 7 to 9 |
| dew | −8 to +20 | 7 to 28 |
| water | −4 to +90 | 28 to 31 |
| frost | −8 to +2 | 35 to 52 |
| ice | −12 to +2 | 48 to 59 |

E. Frost/Ice and Thickness Discrimination Tests

If the insertion loss measurement is made at fixed frequency within the SAW passband, the sensor's response to frost and ice can be more easily distinguished.

Table 3 shows the ability of the SAW phasechange sensor to distinguish various frost thicknesses, and to distinguish between frost and ice.

TABLE 3

| LAYER THICKNESS INSERTION-LOSS MEASUREMENTS | | |
|---|---|---|
| Condition | Temp. (°C.) | Insertion Loss (dB) @ 74 MHz |
| air | −4 | 8.2 |
| 0.05 mm frost | −4 | 40.4 |
| 0.5 mm frost | −4 | 48.9 |
| 2.0 mm frost | −4 | 52.5 |
| 3.0 mm ice | −4 | 59.2 |
| 3.0 mm water | −4 | 30.2 |

With the vapor source off and a tight glass cover on the flatpack to prevent condensation, the dry sensor was chilled to −4° C. The insertion loss at 74.0 MHz was 8.2 dB.

With the vapor source off and the flatpack open to room air, the dry sensor was chilled to −4° C. A thin noncontinuous layer of dew grew on the sensor surface and then froze. The layer thickness of frost was approximately 0.05 mm. The insertion loss at 74.0 MHz was 40.4 dB.

The vapor source was turned on to grow a thicker frost layer. Growth was continued at −4° C. to reach an approximate layer thickness of 0.5 mm before the vapor source was turned off. The insertion loss increased to 48.9 dB at 74 MHz.

More frost was deposited at −4° C. using the vapor source until approximate thickness was 2 mm. The insertion loss increased to 52.5 dB at 74 MHz.

An ice layer about 3 mm thick on the sensor was formed by filling the flatpack with distilled water and chilling quickly to −4° C. The insertion loss was 59.2 dB at 74 MHz. For comparison, a bulk water layer about 3 mm thick was obtained by filling the horizontal flatpack to form a large meniscus. By slow chilling, the water was supercooled down to −4° C. and the sensor insertion loss was 30.2 dB at 74 MHz.

It can be seen that, at constant temperature, the sensor's insertion loss rapidly increases with frost deposition and then approaches a limiting value as frost thickness increases. The insertion loss due to ice is still about 6 dB larger than that from frost. The insertion loss due to water is at least 10 dB less than that from frost.

F. Impedance Change Tests

An alternative to insertion loss is the use of electrical reflection measurements from a single IDT of the SAW phase-change sensor. Either input impedance $Z^*(\omega)$ or input admittance $Y^*(\omega) = 1/Z^*(\omega)$ can be obtained, with admittance being preferred for SAW device input properties. $Y^*$ is a complex quantity $Y^* = Y' + Y''$; one can obtain either the real or imaginary part with the identifications $Y'(\omega) = G(\omega)$ and $Y''(\omega) = \omega C(\omega)$, where $G(\omega)$ is "radiation conductance" and $C(\omega)$ is "electrostatic capacitance" of the input IDT at frequencies within the SAW passband. The quantity $\omega$ is $2\pi$ times frequency.

Input measurements of $G(\omega)$ and $C(\omega)$ for a SAW phase-change sensor were made with various water deposits. At suitable fixed frequency, the radiation conductance $G(\omega)$ is very sensitive to the water phase-change, as shown by Table 4.

TABLE 4

| MEASUREMENTS USING IMPEDANCE | | |
| --- | --- | --- |
| Condition | Temp. (°C.) | $G(\omega)$, millisiemens @ 72.7 MHz |
| air | 20.0 | 131.9 |
| bulk water | −4.6 | 108.0 |
| frost | −4.6 | 60.0 |
| bulk ice | −4.6 | 12.0 |

Table 4 shows that separation between frost and bulk ice using impedance measurement is much wider than is the case for the insertion loss measurements. In addition to these large changes in input conductance at fixed frequency, the frequency peak value changes greatly. For example, maximum conductance shifts from 72.7 MHz (air loading) to 72.3 MHz (frost); to 71.4 MHz (bulk water); and to 70.3 MHz (bulk ice).

The invention has been described above with particularity so as to teach one skilled in the art how to make and use the invention. Many modifications will fall within the scope of the invention. For instance:

Any non-corroding, highly conductive, adherent, low-contact-resistance, thermal-expansion compatible, bondable metallization system useable with thin-film deposition, patterning and etching to required IDT dimensions can be substituted for Cr/Au.

Any chemically inert piezoelectric substrate capable of crystallographic orientation, surface finishing and withstanding photolithographic processing can be substituted for the 128Y-X $LiNbO_3$. However, the strong piezoelectric coupling coefficient ($K^2 = 0.052$) and low acoustic loss ($\alpha \sim 0.01$ dB/cm-MHz) of this material result in SAW sensors with a low unloaded insertion loss (7 to 9 dB at 75 MHz), high sensitivity to deposited mass and hence large changes in insertion loss with frost deposition. The added insertion loss due to frost loading should roughly scale linearly with $K^2$, other factors being equal.

Any hydrophobic surface treatment compatible with the sensor materials may be used, although that used in the disclosed sensor contributes no measurable insertion loss and is thus preferred.

The acoustic path length may be varied in order to adjust the total insertion loss with frost/ice/water loading. Reduced path length would reduce loaded insertion loss roughly linearly with length, other factors being equal but also would reduce sensitivity to phase-change and introduce substantial acoustical reflections between IDT's.

The IDT period $\lambda$ may be altered in order to adjust operating frequency to lower or higher values, which may affect loaded insertion loss sensitivity.

Several other thermally conductive package configurations may be chosen. However, a flatpack allows excellent thermal contact to be achieved between the sensor and the cold surface, along with excellent corrosion resistance, electrical and mechanical stability and low parasitic capacitance. Electrical connection to the thermally conductive package may be obtained by means other than wirebonds.

What is claimed is:

1. A surface acoustic wave $H_2O$ phase-change sensor comprising:
   (a) a piezoelectric substrate;
   (b) metallization patterns fabricated on said piezoelectric substrate to form an input interdigitated transducer and an output interdigitated transducer;
   (c) electrical connectors connected to said metallization patterns;
   (d) a hydrophobic surface treatment covering said metallization patterns to form a sensing surface; and
   (e) means for detecting and discriminating between at least water, frost and ice on said sensing surface, said means including said piezoelectric substrate configured to have a thickness to acoustical wavelength ration of 9 or higher.

2. A surface acoustic wave $H_2O$ phase-change sensor as defined by claim 1 wherein said piezoelectric substrate is composed of lithium niobate cut with substantially 128 degree Y rotation.

3. A surface acoustic wave $H_2O$ phase-change sensor as defined by claim 1 wherein said interdigitated transducers are oriented for substantially X-propagation of surface acoustic waves.

4. A surface acoustic wave $H_2O$ phase-change sensor as defined by claim 1 wherein said metallization patterns are composed of RF-diode sputtered Cr/Au.

5. A surface acoustic wave $H_2O$ phase-change sensor as defined by claim 1 wherein said input interdigitated transducer has 10 finger pairs, said output interdigitated transducer has 30 finger pairs, and said unput interdigitated transducer to said output interdigitated transducer center-to-center spacing is substantially 30 acoustical wavelengths.

6. A surface acoustic wave $H_2O$ phase-change sensor as defined by claim 1 wherein said thermally conductive package is composed substantially of gold-plated nickel.

7. A surface acoustic wave $H_2O$ phase-change sensor as defined by claim 1 wherein said hydrophobic surface treatment is a polysiloxane derivatizer.

8. A surface acoustic wave $H_2O$ phase-change sensor as defined by claim 1 wherein said sensor operates at about 75 MHz.

9. A surface acoustic wave $H_2O$ phase-change sensor as recited in claim 1, further comprising:
(f) a thermally conductive package; and
(g) means for thermally coupling said thermally conductive package to said piezoelectric substrate.

10. A surface acoustic wave $H_2O$ phase-change sensor as recited in claim 9, wherein said thermally coupling means comprises a thermally conductive adhesive attaching said thermally conductive package to said piezoelectric substrate.

11. A method of detecting $H_2O$ phase changes comprising the steps of:
(a) exposing a surface acoustic wave device with a hydrophobic sensing surface so that various $H_2O$ phases form on said hydrophobic sensing surface:
(b) measuring an electrical parameter from said surface acoustic wave device; and
(c) determining from said electrical parameter whether said various $H_2O$ phases are air, water, frost, dew, or ice.

12. A method of detecting $H_2O$ phase changes as defined by claim 11 wherein said electrical parameter is insertion loss.

13. A method of detecting $H_2O$ phase changes as defined by claim 11 wherein said electrical parameter is radiation conductance.

14. A method of detecting $H_2O$ phase changes as defined by claim 11 further comprising the step of determining from said electrical parameter a thickness of said various $H_2O$ phases formed on said hydrophobic sensing surface.

15. A method of detecting $H_2O$ phase changes as defined by claim 11 further comprising the step of orienting said hydrophobic sensing surface so that gravity will remove water from said hydrophobic sensing surface.

16. A surface acoustic wave $H_2O$ phase-change sensor comprising:
(a) a piezoelectric substrate;
(b) metallization patterns fabricated on said piezoelectric substrate to form an input interdigitated transducer and an output interdigitated transducer;
(c) electrical connectors connected to said metallization patterns;
(d) a hydrophobic surface treatment covering said metallization patterns to form a sensing surface; and
(e) means for detecting and discriminating between at least air, water, frost, dew and ice on said sensing surface, said means including said piezoelectric substrate configured to have a thickness to acoustical wavelength ratio of 9 or higher.

17. A surface acoustic wave $H_2O$ phase-change sensor as recited in claim 16, further comprising:
(f) a thermally conductive package;
(g) means for thermally coupling said thermally conductive package to said piezoelectric substrate.

18. A surface acoustic wave $H_2O$ phase-change sensor comprising:
(a) a piezoelectric substrate:
(b) metallization patterns fabricated on said piezoelectric substrate to form an input interdigitated transducer and an output interdigitated transducer;
(c) electrical connectors connected to said metallization patterns;
(d) a thermally conductive package;
(e) means for thermally coupling said thermally conductive package to said piezoelectric substrate; and
(f) a hydrophobic surface treatment covering said metallization patterns to form a sensing surface;
(g) said piezoelectric substrate having a thickness to acoustical wavelength ratio of 9 or higher.

19. A surface acoustic wave $H_2O$ phase-change sensor as recited in claim 18, further comprising:
(h) a thermally conductive package;
(i) means for thermally coupling said thermally conductive package to said piezoelectric substrate.

20. A method of detecting $H_2O$ phase changes comprising the steps of:
(a) providing an interdigitated piezoelectric surface acoustic wave device with a hydrophobic surface treatment, said acoustic wave device having a thickness to acoustical wavelength ratio of 9 or higher;
(b) exposing the treated surface of the acoustic wave device so that various $H_2O$ phases form on the treated surface;
(c) measuring an electrical parameter from said surface acoustic wave device; and
(d) determining from said electrical parameter whether said various $H_2O$ phases are water, frost or ice.

21. The method as recited in claim 20 further comprising the steps of:
(e) thermally and mechanically coupling said surface acoustic wave device to a thermally conductive package so that said treated surface is exposed; and
(f) positioning the thermally conductive package to a component of a system desired to be monitored.

22. The method as recited in claim 20 further comprising the step of determining from said electrical parameter whether said various $H_2O$ phases are air, water, dew, frost or ice.

* * * * *